United States Patent [19]
Sayer

[11] 3,938,383
[45] Feb. 17, 1976

[54] METHOD AND APPARATUS FOR DETECTING THE THERMAL CHARACTERISTICS OF A SUBSURFACE FORMATION IN SITU

[76] Inventor: Wayne L. Sayer, 2851 N. Inyo St., Bakersfield, Calif. 93305

[22] Filed: Sept. 19, 1974

[21] Appl. No.: 507,275

[52] U.S. Cl. .................................. 73/154; 73/15 A
[51] Int. Cl.² .......................................... E21B 47/06
[58] Field of Search .................. 73/154, 15 A, 15 R

[56] References Cited
UNITED STATES PATENTS
3,805,587  4/1974  Sayer ............................... 73/154 X Primary Examiner—Jerry W. Myracle
Attorney, Agent, or Firm—Huebner & Worrel

[57] ABSTRACT

A method and apparatus for detecting the thermal characteristics of a subsurface formation in situ wherein a borehole has been drilled from the earth's surface, including inserting a known volume of cryogenic material into the borehole to a predetermined position in the formation to produce a zone of cooling in the formation thereabout; conducting test energy, subject to change by passage through a cooled medium of conduction, from a predetermined position in the borehole below the zone of cooling along a plurality of paths through and laterally of the zone to the surface; sensing the changes in the energy incident to passage through the zone at predetermined positions on the surface laterally of the borehole; calculating the volume of the zone from the known and acquired information to determine the thermal conductivity of the formation; and noting the time required for the known volume of cryogenic material to be boiled off by the formation to determine the latent heat of the formation.

29 Claims, 11 Drawing Figures

METHOD AND APPARATUS FOR DETECTING THE THERMAL CHARACTERISTICS OF A SUBSURFACE FORMATION IN SITU

BACKGROUND OF THE INVENTION

The present invention relates to a method and apparatus for detecting the thermal characteristics of a subsurface formation in situ and more particularly to such a method and apparatus adapted to obtain reliable data concerning the thermal conductivity, latent heat and general thermal characteristics of subsurface soil and rock strata in place by the insertion of cryogenic material into the formation without having to follow the conventional practice of taking core samples from which only a very rough approximation of such information can be derived.

A reliable determination of the thermal characteristics of subsurface rock and soil formations is important in many areas of application. Geological studies preparatory to mining, oil well drilling, geothermal prospecting and the like depend significantly on a variety of types of information including the characteristics of thermal conductivity and latent heat in subsurface formations of rock strata and soil. Heretofore, there has been no accurate method and/or apparatus for gathering this information.

Conventional practice calls for the extraction of one or more core samples from the formation under study and the subsequent analysis of such core samples in an effort to determine what the characteristics of the formation are. The information derived form such analysis constitutes merely an educated guess and is unreliable to the extent of being virtually worthless. The major difficulty is that extraction of such core samples usually destroys the crystalline structure of the rock within the sample or causes the soil to lose its integrity thereby precluding observation of the sample in its natural form. Additionally, the extraction of core samples permits the latent heat of the samples to be influenced and therefore changed by passage through other formations during extraction and by subjection to the atmosphere upon removal from the earth.

The applicant's U.S. Pat. No. 3,805,587 entitled "Method And Apparatus For Locating Geothermal Sources Of Energy" discloses a method and apparatus having the capability of determining the location of a subterranean geothermal anomaly. It would be advantageous in the use of the method and apparatus of that patent to have a reliable means for determining the thermal conductivity and latent heat of subsurface formation for use in providing additional information to assist in more accurately determining the depth below the earth's surface of the geothermal anomaly.

Therefore, it has long been recognized that it would be desirable to have a method and apparatus for detecting the thermal characteristics of a subsurface formation in situ without having to extract core samples which do not reflect the natural structure of the rock, latent heat of the formation, and which otherwise fail to provide reliable data useful in conducting geological surveys for a variety of purposes.

SUMMARY OF THE INVENTION

It is therefore an object of the present invention to provide a method and apparatus for detecting the thermal characteristics of a subsurface formation.

Another object is to provide such a method and apparatus which have particular utility in the determination of the thermal conductivity and latent heat of a subsurface formation.

Another object is to provide such a method and apparatus which permit such detection to be performed with an accuracy and reliability not achievable prior to the present invention.

Another object is to provide such a method and apparatus which permit such detection to be performed in situ.

Another object is to provide such a method and apparatus which eliminate the necessity for extracting a core sample from a subsurface formation subject to examination of its thermal characteristics.

Another object is to provide such a method and apparatus which do not require that the information be acquired from a core sample wherein typically the natural crystalline structure of rock and the natural integrity of soil within the sample is destroyed or otherwise altered.

Another object is to provide such a method and apparatus which are adaptable for use in a variety of operative environments and wherein the information gathered is usable in achieving a variety of operational objectives.

Another object is to provide such a method and apparatus which can be employed at a commercially feasible cost.

A further object is to provide such a method and apparatus which can be modified in a variety of respects to meet the particular requirements of the survey being conducted and the physical structure of the formation being studied.

Further objects and advantages are to provide improved elements and arrangements thereof in an apparatus for the purposes described which is dependable, economical, durable and fully effective in accomplishing its intended purposes.

DESCRIPTION OF THE FIRST FORM

Figure 1:
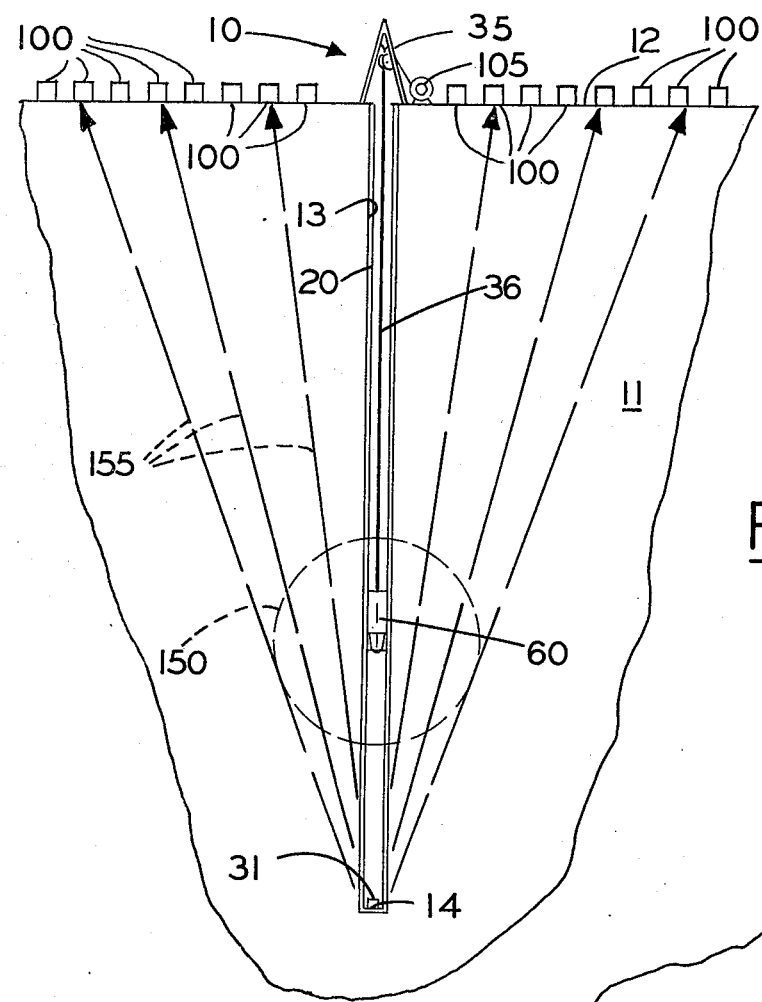
FIG. 1 is a schematic vertical section of the apparatus of the first form of the present invention showing it in its operative environment within the earth.

Referring more specifically to the drawings, an apparatus 10 embodying the principles of the first form of the present invention is shown in its operative environment in FIG. 1. The earth is indicated at 11 and the earth's surface at 12. A borehole 13, having a lower end 14, is formed in the earth, as by drilling, to permit installation of a portion of the apparatus therein. No specific representation of a distinct formation is shown in the drawings since, in its most frequent application, the formation under study is simply the earth at a given depth below a given position on the earth's surface. The formation under study can, of course, be of any composition including rock, sand, soil or the like and be located at a depth limited only to the capability of drilling tools to reach the specific depth involved. Thus, the optimum depth selected for the borehole will depend on the specific information being sought. However, the formation selected for analysis should normally be of a depth at least sufficient to prevent influence by surface temperatures.

Figure 3:
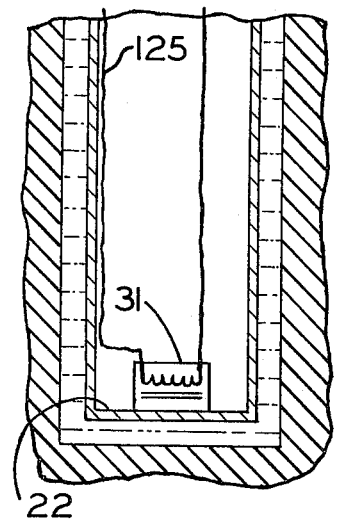
FIG. 3 is a somewhat enlarged fragmentary vertical section of the apparatus.

A casing 20 is inserted in the borehole 13. The casing has a cylindrical side wall 21 and a sealed lower end 22. The casing is preferably of a diameter somewhat smaller than that of the borehole and is preferably insulated against both thermal and electrical conductivity. An annular ring 23 constructed of a suitable, highly thermally conductive material such as copper, aluminum or the like is mounted on the side wall of the casing and extends therethrough to communicate with the exterior of the casing, as best shown in FIG. 3. The ring has a conical interior surface 24 bounding a central passage 25 extending substantially axially of the casing. The passage is tapered in the direction of the lower end 22 of the casing and the ring is disposed in spaced relation thereto. The optimum distance between the lower end of the casing and the ring depends, in part, upon the characteristics of thermal conductivity of the earth 11 adjacent to the borehole. Knowledge of the specific distance utilized is employed in calculations involved in the practice of the method of the present invention, as will be seen. As shown in FIG. 3, a readily freezable fluid 26, such as water, is deposited in the borehole about the casing so as to fill the borehole well above the location of the annular ring in the casing. In many instances the drilling fluid produced during drilling of the borehole can be utilized for this purpose.

A spring type electrical contact 30 is fastened on the cylindrical side wall 21 of the casing 20 immediately below the annular ring 23 so as to extend transversely of the axis defined by the passage 25. A suitable test energy conducting device or transmitter 31 is mounted within the casing on the sealed lower end 22 thereof. The transmitter can be of a variety of types capable of transmitting a suitable form of test energy such as electrical current, or compression waves in the form of sound or vibratory energy. Devices such as piezoelectric or magnetostrictive transducers are believed to be suitable for the purpose of transmitting compression waves. A simple electrode can be employed to discharge electrical current. In any case, the transmitter preferably should communicate with the exterior of the casing through the sealed lower end 22 thereof to permit optimum transmission of the test energy therefrom. Although a probe can be employed to make direct contact between the transmitter and the lower end 14 of the borehole, the presence of the fluid 26 therebetween is sufficient to insure conduction of the test energy between the transmitter and the earth.

Figure 4:
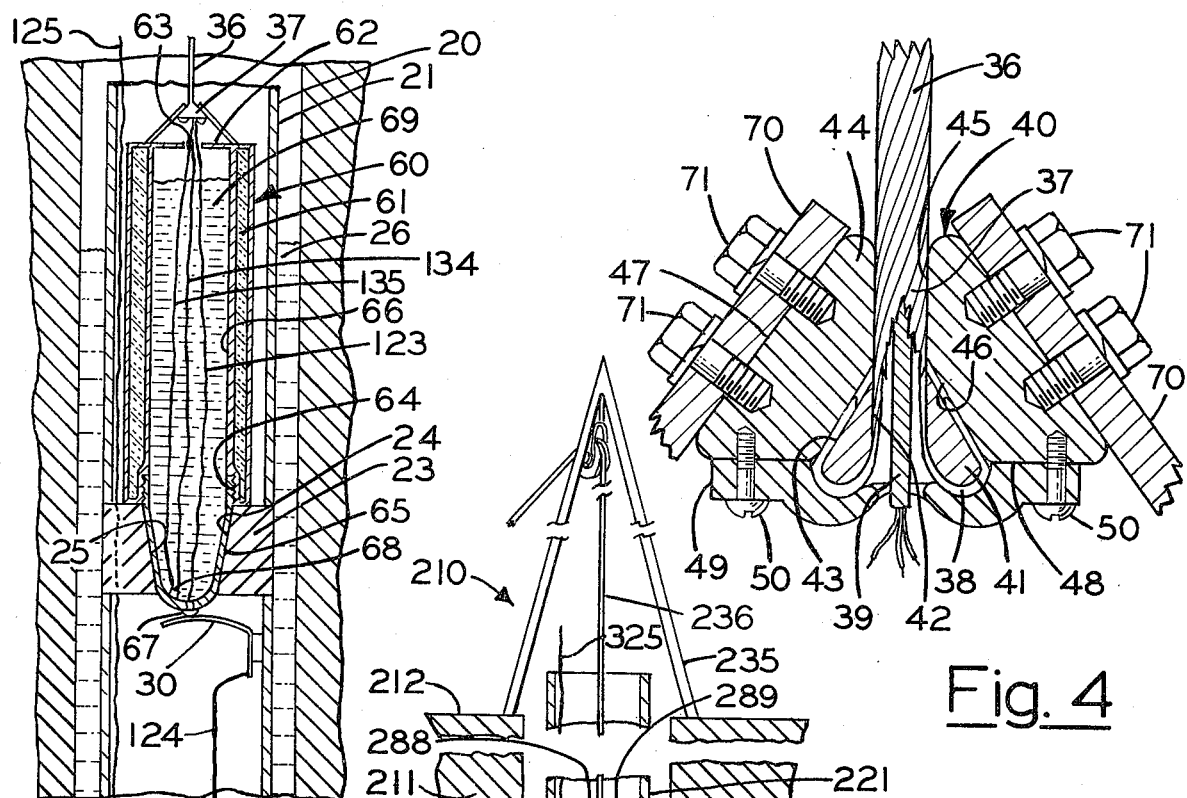
FIG. 4 is a somewhat further enlarged fragmentary vertical section of a mounting assembly of the apparatus.

As shown in FIG. 1, a suitable hoist assembly 35 is mounted on the earth's surface 12 over the borehole 13 and supports an elongated cable 36 having a work end 37 adapted to be lowered down the borehole internally of the casing 20 by the hoist assembly. The cable preferably has a reinforced external sheath 38 enclosing a central core 39, as shown in FIG. 4.

A mounting assembly 40 is borne by the work end 37 of the cable 36. The mounting assembly is composed of a central ring 41 having an axial bore 42 extending therethrough and a conical exterior surface 43. The work end of the cable is extended through the bore 42 of the ring and the sheath 38 is stretched outwardly over the exterior surface of the ring. An external ring 44, having an axial bore 45 and a conical internal surface 46, is positioned with the cable extending through its axial bore and the central ring nested against the internal surface 46 with the sheath disposed in binding engagement therebetween. The external ring has a conical external surface 47 and a bottom surface 48. A retaining plate 49 is secured on the bottom surface of the external ring by bolts 50. The work end of the cable 36 thus securely supports the mounting assembly 40 with the core 39 of the cable extending axially through the assembly and out through the retaining plate, as shown in FIG. 4. It will be seen that the cable and mounting assembly could have a variety of other specific configurations without departing from the invention. However, the specific structure described is believed to be advantageous for purposes of ease of operation.

A vessel 60 is adapted to be mounted in depending relation on the mounting assembly 40 thereby supporting the vessel on the work end 37 of the cable 36. The vessel has a thermally insulated cylindrical portion 61. This portion of the vessel is insulated to preserve the temperature of material deposited therein. The cylindrical portion has an end wall 62 extending transversely of one end thereof. The end wall has a vent 63. The cylindrical portion has an internally screw-threaded opposite end 64. The vessel has a heat conductive portion 65 which is screw-threadably mounted in the opposite end 64 of the cylindrical portion in fluid sealing relation, as best shown in FIG. 3. The heat conductive portion may be constructed of any suitably heat conductive material such as copper, aluminum, silver, or the like. The cylindrical portion and the conductive portion of the vessel form an interior chamber 66 for the vessel.

An electrical contact 67 is mounted in the conductive portion 65 of the vessel 60 extending therethrough so as to protrude endwardly from the conductive portion of the vessel. A pressure transducer 68 is fastened on the conductive portion of the vessel within the chamber. The transducer can be of any suitable type adapted to register when fluid material received in the chamber of the vessel has been dissipated for purposes of the practice of the method of the present invention. As shown in FIG. 3, the vessel is adapted to receive a selected quantity of cryogenic material 69. Such substances as liquid nitrogen, liquid helium and liquid argon are excellently suited for this purpose in that they have extremely low temperatures and are caused to boil off or vaporize when subjected to higher temperatures.

A pair of metal straps 70 are mounted on the end wall 62 of the vessel 60 and extended in converging relation endwardly therefrom. The straps are mounted on the external ring 44 of the mounting assembly 40 by bolts 71, as best shown in FIG. 4. Thus, the vessel is suspended from the work end 37 of the cable 36 in substantially axial alignment therewith.

Figure 5:
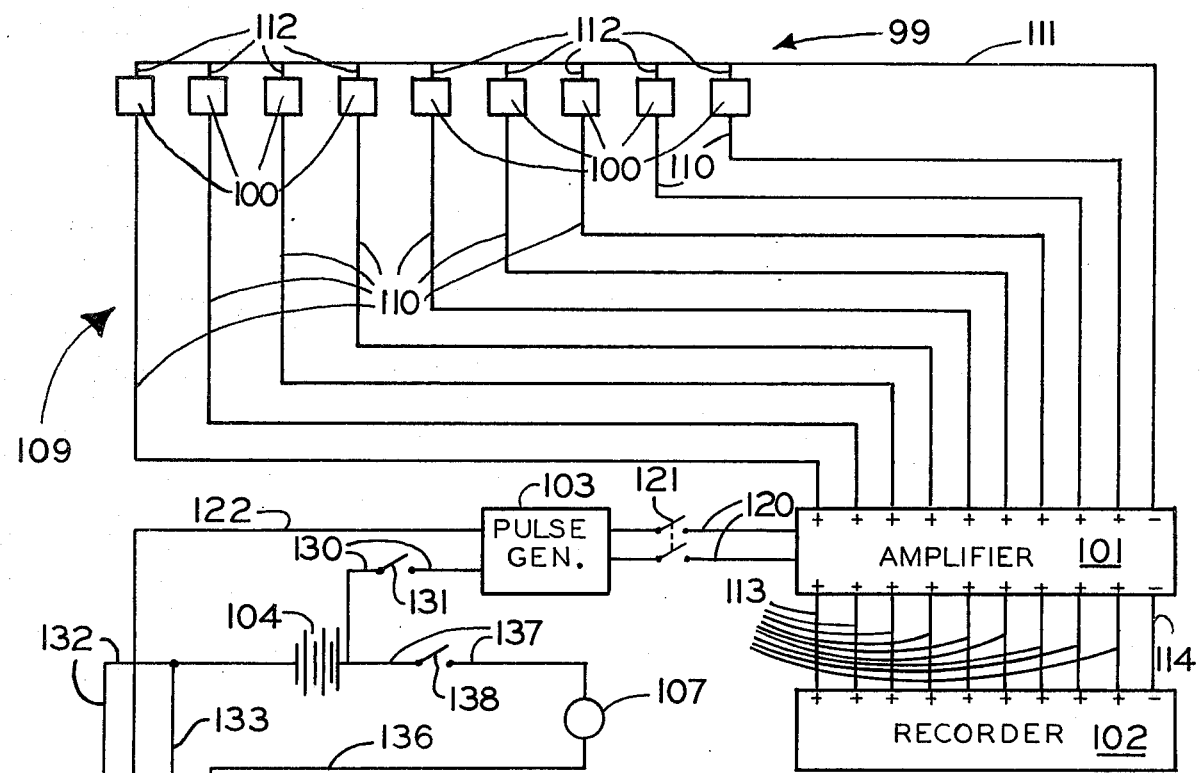
FIG. 5 is a schematic diagram of the apparatus showing the electrical circuit thereof.

The apparatus 10 utilizes an array of detection equipment 99 shown in the schematic diagram in FIG. 5. The equipment includes a plurality of sensors or receivers 100 adapted to receive the specific form of test energy discharged by the transmitter 31. Where electrical current is transmitted, receivers utilizing electrodes can be employed. Where compression waves such as sound are transmitted, geophones or receiving transducers can be employed as receivers. The specific number of such receivers employed depends upon the demands of the study being conducted. For purposes of precision, normally more receivers than those shown in FIG. 5 are used. To provide the optimum performance, the receivers are preferably individually adjustable for control of the sensitivity of the receiver to the test energy to be received.

The apparatus 10 has a multichannel amplifier 101 having a capacity sufficient for individual amplification of the energy detected by each of the receivers 100. The apparatus further includes a multichannel recorder 102 adapted individually to record the intensity of the energy detected by the receivers. The recorder can be of any suitable type such as a strip chart recorder which produces a strip chart bearing individual notation of the detected signals. The receivers, amplifier and recorder are powered by a suitable power source, not shown.

The apparatus further includes a pulse generator 103 adapted to supply a pulse of electrical current to the transmitter 31 and to the amplifier 101 and recorder 102. The pulse generator can either be of a type adapted to be operated to discharge a single pulse of current upon command, also as by closing a switch not shown, or of a type adapted to operate sequentially for as long as power is supplied to it. The purpose for such pulse generation will subsequently become more clearly apparent.

A battery 104 is provided to supply power to the pulse generator 103 and portions of the apparatus 10 yet to be described since the apparatus is frequently used in relatively remote areas. The hoist assembly 35 has a commutator 105, having three individual brush type electrical connections 106 for purposes subsequently to be described. A pressure readout gauge 107 is included in the detection equipment adapted to register the pressure detected by the pressure transducer 68.

The detection equipment 99 includes an electrical circuit 109, shown in FIG. 5. The circuit provides a plurality of electrical conductors 110 individually extended from each of the receivers 100 and connected to the multichannel amplifier 101. The circuit is completed between the amplifier and the receivers by electrical conductors 111 and 112 extending therebetween. Thus, the receivers are electrically connected in parallel to each other and in series with the amplifier. A plurality of electrical conductors 113 individually connect the amplifier 101 with the recorder 102. Electrical conductor 114 interconnects the recorder with the amplifier thus completing the circuit through the recorder. Therefore, the receivers, amplifier and recorder are linked in series and the receivers individually in parallel through this portion of the circuit.

The pulse generator 103 is electrically connected to the amplifier 101 by a pair of conductors 120. The conductors are interrupted by a master control switch 121 operable to open and close the circuit through conductors 120. Electrical conductor 122 extends from the pulse generator to the brush type electrical connection 106 of the commutator 105, on the left as viewed in FIG. 5. Electrical conductor 123 extends through the core 39 of the cable 36 from the selected connection of the commutator to electrical contact 67 borne by the heat conductive portion 65 of the vessel 60. Electrical conductor 124 extends from the spring contact 30 and is connected to the transmitter 31. Electrical conductor 125 extends from the transmitter upwardly through the casing 20, as best shown in FIG. 3.

Electrical conductor 130 interconnects the pulse generator 103 and the battery 104 having a switch 131 intermediate thereof for selected opening and closing of the circuit 109 through conductor 130. Electrical conductor 132 interconnects the battery and conductor 125. Electrical conductor 133 interconnects conductor 132 and the connection 106 of the commutator 105 in the center as viewed in FIG. 5. Conductor 134 interconnects the same connection 106 and the pressure transducer 68 extending with conductor 123 through the core 39 of the cable 36. Electrical conductor 135 interconnects the pressure transducer and the electrical contact 106 of the commutator 105 on the right as viewed in FIG. 5 extending back through the core of the cable. Electrical conductor 136 interconnects the same electrical contact of the commutator with the pressure readout gauge 107. Electrical conductor 137 interconnects the pressure readout gauge and conductor 130 to complete this portion of the circuit through the battery. Thus, the battery, pressure transducer and pressure readout gauge are connected in series relation. A switch 138 is interposed in conductor 137 and is operable to open and close this portion of the circuit through the conductor.

For illustrative convenience, a zone of cooling is represented at 150 and a plurality of paths of test energy at 155 in FIG. 1 the significance of which will become apparent.

DESCRIPTION OF THE SECOND FORM

Figure 7:
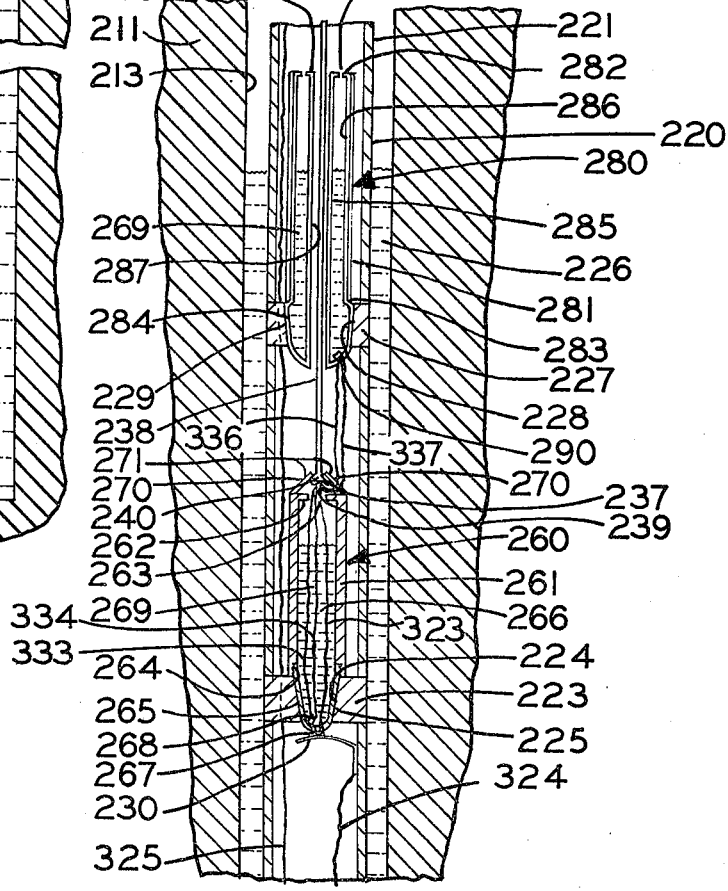
FIG. 7 is a somewhat enlarged fragmentary vertical section of the apparatus shown in FIG. 6.
Figure 6:
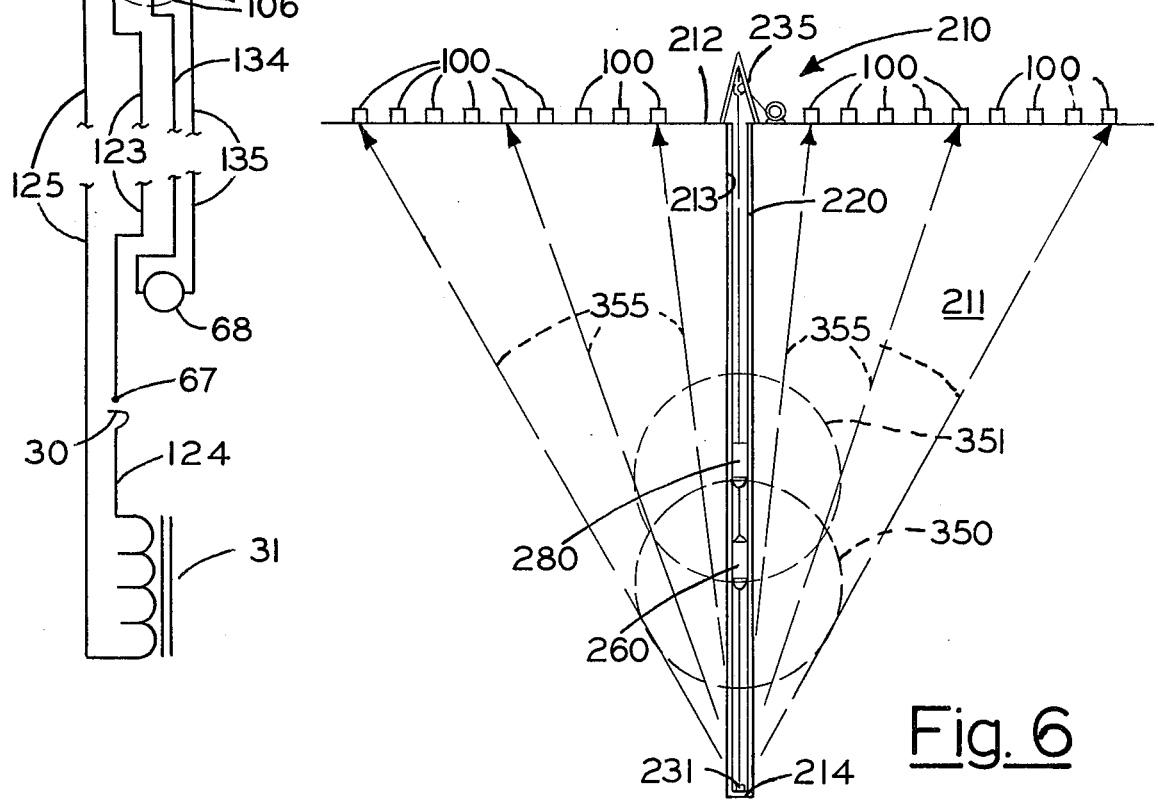
FIG. 6 is a schematic vertical section of the apparatus of the second form of the present invention showing it in its operative environment within the earth.
Figure 8:
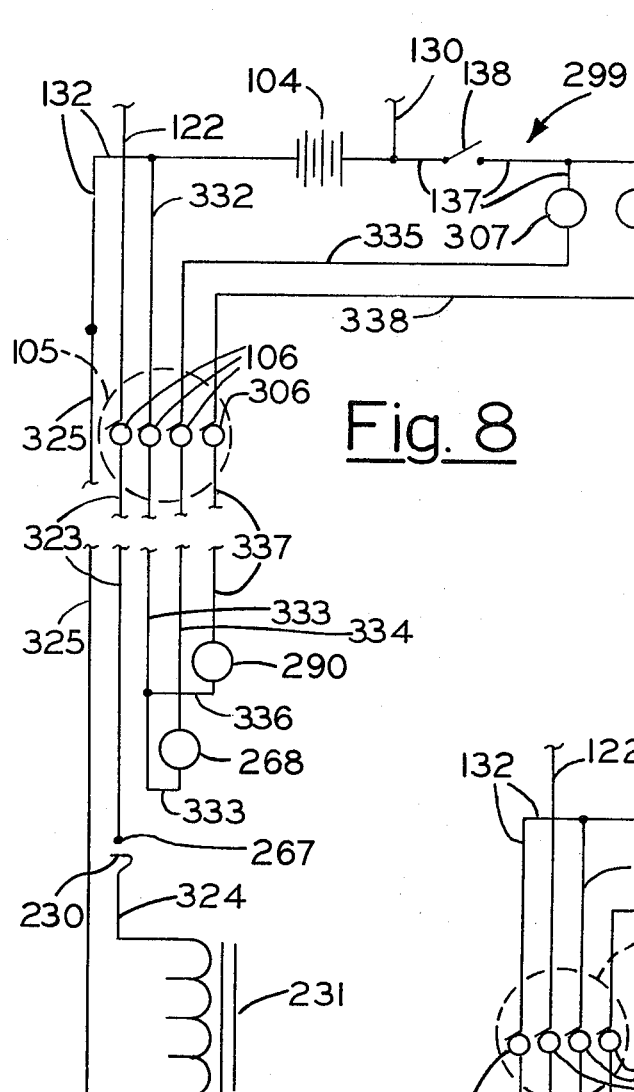
FIG. 8 is a fragmentary schematic diagram of the portion of the electrical circuit of the apparatus of the second form of the present invention which varies from the circuit of the first form of the invention shown in FIG. 5.

The apparatus 210 constituting the second form of the present invention is shown in FIGS. 6, 7 and 8. The earth is represented at 211 with the earth's surface identified by the numeral 212. A borehole 213 is formed in the earth having a lower end 214. As previously noted, the optimum depth for the borehole depends upon the location of the specific formation to be studied and the test information required.

The apparatus 210 is in many respects identical to apparatus 10. Thus, the apparatus 210 has a casing 220 with a cylindrical side wall 221 and a sealed lower end 222. The casing is positioned in the borehole 213 and preferably has a diameter somewhat smaller than that of the borehole. A first annular ring 223, having a conical interior surface 224 defining a central passage 225 of predetermined diameter, is mounted on the side wall of the casing extending transversely of the casing to position the interior surface substantially concentric to the casing. The ring is positioned in spaced relation from the lower end 222 of the casing. A readily freezable fluid 226 is shown in FIG. 7 extending about the casing to a predetermined level in the borehole.

Apparatus 210 differs from apparatus 10 in that it has a second annular ring 227, having a conical interior surface 228 defining a central passage 229 of a predetermined, substantially larger diameter than that of the first annular ring, mounted on the side wall of the casing in spaced relation to and above the first annular ring and extending transversely of the casing so as to position the interior surface in substantial axial alignment with that of the first annular ring 223. The optimum spaced relationship between the first annular ring and the lower end of the casing, between the first annular ring and the second annular ring and the difference in the diameters of the central passages of the rings will subsequently be described.

As in apparatus 10, apparatus 210 has a spring type electrical contact 230 mounted on the side wall 221 of the casing 220 between the first annular ring 223 and the sealed lower end 222 of the casing extending in juxtaposition and in substantially right-angular relation to the central passage 225. A suitable energy conducting means or electrical current transmitter 231 is mounted within the casing on the sealed lower end 222 thereof. As in the first form of the invention, the transmitter could, of course, be of any suitable type adapted to conduct test energy such as electrical current or compression waves such as sound into the earth from the lower end 214 of the borehole 213.

A suitable hoist assembly 235 is mounted on the earth's surface 212 extending over the borehole 213. The hoist assembly mounts a cable 236, having a work end 237, and is adapted to lower the work end of the cable down the borehole within the casing 220. The cable is composed of an outer sheath 238 enclosing a central core 239. The work end of the cable mounts a mounting assembly 240 identical to mounting assembly 40 of apparatus 10, as shown in FIG. 4.

A first vessel 260 virtually identical to vessel 60 of apparatus 10 is mounted on the work end 237 of the cable 236. The vessel consists of an insulated cylindrical portion 261 having an end wall 262 mounted on one end thereof with a central vent 263. The cylindrical portion has an internally screw-threaded opposite end 264 mounting in screw-threaded fluid sealing relation a heat conductive portion 265 to define an interior chamber 266 for the vessel. An electrical contact 267 is fastened on and extends through the heat conductive portion of the vessel and a first pressure transducer 268 is borne by the heat conductive portion within the chamber. A suitable cryogenic material 269, such as those described in regard to the first form of the invention, is shown in FIG. 7 received in the vessel. A pair of metal straps 270 are mounted on the end wall 262 and extend upwardly in convergent relation. The straps are mounted on the mounting assembly 240 by bolts 271 so as securely to mount the vessel 260 on the work end of the cable.

In variance from apparatus 10, apparatus 210 has a second vessel 280 slidably mounted on the cable 236 above the first vessel 260. The second vessel is composed of an insulated cylindrical portion 281, having an integral inwardly extending annular lip 282 at one end thereof and an opposite end 283 with a heat conductive portion 284 mounted on the opposite end of the cylindrical portion. Integral with the heat conductive portion is an internal cylindrical wall 285 extending upwardly inwardly concentric to the cylindrical and heat conductive portions of the second vessel so as to define a cylindrical chamber 286 between the wall and the cylindrical portion 281. Wall 285 also defines a central passage 287 extending axially through the vessel. The second vessel is slidably mounted on the cable with the cable extending through the central passage 287, as shown in FIG. 7. The cylindrical wall has an annular outwardly extending lip 288 thereby defining an annular vent 289 between lips 282 and 288. A second pressure transducer 290 is fastened on the conductive portion of the second vessel within the chamber 286. As shown in FIG. 7, the second vessel is filled with a predetermined quantity of cryogenic material 269.

Apparatus 210 utilizes detection equipment 299 which is virtually identical to detection equipment 99 of the first form of the present invention and reference is made to FIG. 5 and the description thereof for disclosure of the portion of such equipment common to both forms of the invention. Detection equipment 299 differs from equipment 99 only insofar as necessary to provide for the second pressure transducer 290 thus requiring the modified portion for the circuit 109 shown in FIG. 8 which takes the place of the equivalent portion shown in FIG. 5. Commutator 105 in the case of apparatus 210 mounts a brush type electrical connection 306 in addition to the three contacts 106. The equipment has first and second pressure readout gauges 307 and 308 respectively.

Electrical conductor 323 interconnects contact 106 of the commutator 105 on the left as viewed in FIG. 8 with contact 267. Electrical conductor 324 interconnects contact 230 and transmitter 231 which in turn is connected to conductor 132 by electrical conductor 325 extending upwardly through the casing 220. Conductor 132 is connected to the central electrical connection 106 by electrical conductor 332. The first pressure transducer 268 is connected to the central and right hand brush type electrical connections 106 as viewed in FIG. 8 in series relation by electrical conductors 333 and 334 respectively. Electrical conductor 335 interconnects the right hand connection 106 and first pressure readout gauge 307 which in turn is connected to conductor 137. Electrical conductor 336 interconnects conductor 333 and the second pressure readout transducer 290. Transducer 290 is connected to connection 306 by electrical conductor 337. The second pressure readout gauge 308 is connected to connection 306 by electrical conductor 338 and to conductor 137 by conductor 339.

Again, for illustrative convenience a first zone of cooling is indicated at 350 and a second zone of cooling at 351 in FIG. 6. A plurality of paths of test energy are indicated at 355.

DESCRIPTION OF THE THIRD FORM

Figure 9:
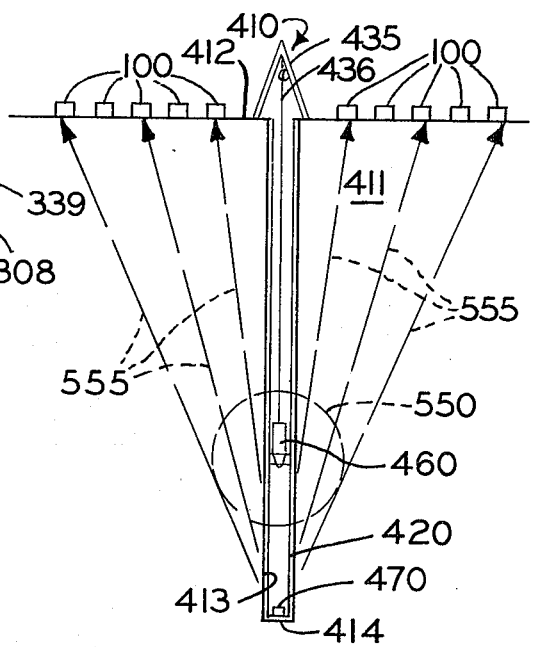
FIG. 9 is a schematic vertical section of the apparatus of the third form of the present invention showing it in its operative environment within the earth.
Figure 11:
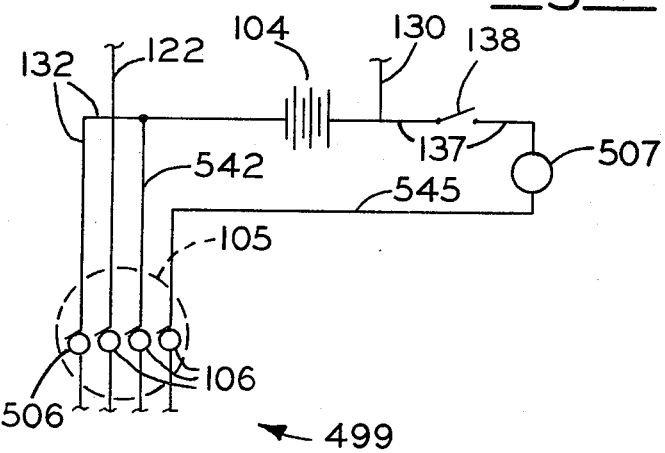
FIG. 11 is a fragmentary schematic diagram of the portion of the electrical circuit of the apparatus of the third form of the present invention which is different from the circuit of the first form of the invention shown in FIG. 5.
Figure 11:
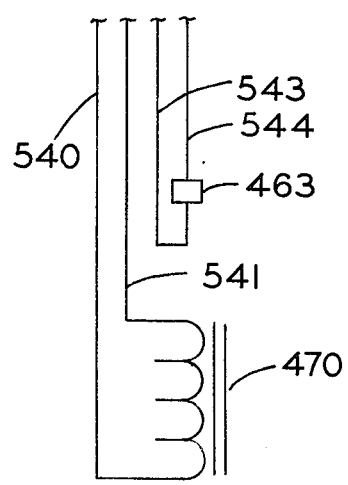
Figure 10:
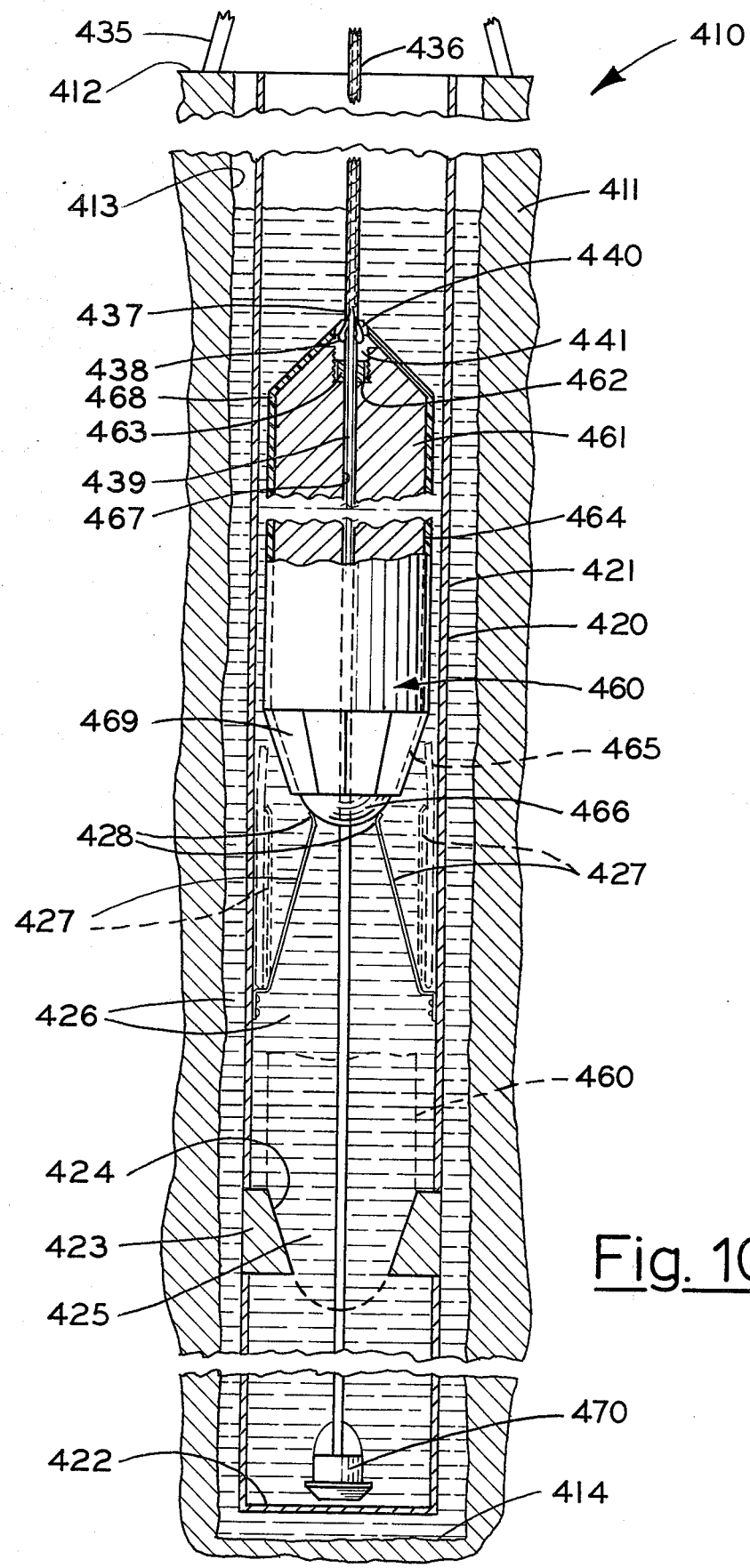
FIG. 10 is a somewhat enlarged fragmentary vertical section of the apparatus shown in FIG. 9.

The apparatus of the third form of the present invention is identified by the numeral 410 and shown in FIGS. 9, 10 and 11. The apparatus is shown in FIG. 9 positioned in the earth 411 with the earth's surface represented at 412. A borehole 413, having a lower end 414, is formed in the earth. Apparatus 410 is, in many respects, identical to apparatus 10 and 210. Thus, the apparatus has a casing 420 having an insulated cylindrical side wall 421 and a sealed lower end 422. A heat conductive annular ring 423, having a conical interior surface 424 bounding a central passage 425, is mounted on the side wall extending transversely of the casing in predetermined spaced relation to the lower end of the casing so as to mount the interior surface 424 substantially concentrically of the casing.

As shown in FIG. 9, a readily freezable fluid 426 fills the borehole 413 and casing 420. Apparatus 410 offers the advantage of being operable even where fluid fills the casing as well as the borehole since, as will be seen, no vent to the surface is required. Thus, in practice the fluid produced during drilling of the borehole can simply be allowed to remain in the borehole and seepage into the casing need not be of concern. A pair of resilient stripping arms 427 are individually mounted on the side wall 421 on opposite sides of the casing above the annular ring. The arms extend in converging relation above and away from the annular ring and have outwardly bent remote ends 428.

A suitable hoist assembly 435 such as hoist assemblies 35 and 235 of the previously described forms of the invention, is mounted on the earth's surface 412 over the borehole 413. The hoist assembly mounts a cable 436, having a work end 437. The cable has a sheath 438 enclosing a core 439. A mounting assembly 440, such as assemblies 40 and 240, is borne by the work end of the cable with the sheath supporting the assembly and the core of the cable extending through the assembly and therebelow a predetermined relatively great distance. The mounting assembly has an externally screw-threaded portion 441 remote from the cable and extending concentrically about the core. As in the previously described forms of the invention, the hoist assembly is selectively operable to lower the mounting assembly down the borehole within the casing and to return it to the surface.

The apparatus 410 has a vessel 460 which varies considerably from the vessels 60 and 260 of the forms of the invention previously described. Vessel 460 has a solid bar 461 constructed of a highly heat conductive metal such as copper, aluminum, silver or the like. The bar has an internally screw-threaded end portion 462 in which is received a suitable temperature sensor 463. The screw-threaded portion 441 of the mount 440 is screw-threaded into the end portion 462 of the bar to mount the bar on the work end 437 of the cable 436 thereby capturing the temperature sensor internally of the bar. The bar has a central cylindrical portion 464 and a tapered conical portion 465 mounting a thermally insulated cap 446 at the remote end thereof. The solid bar is axially pierced by a bore 467 through which the core 439 of the cable is extended, as can best be seen in FIG. 10. The bar is enclosed in a thermally insulating sheath 468 enclosing the bar from the mounting assembly to the insulated cap of the bar. The sheath has a segmented portion 469 which encloses the conical portion 465 of the bar. The segmented portion of the sheath is adapted to be stripped away by the stripping arms 427. An energy conducting means or compression wave transmitter 470 is mounted on the remote end of the core 439 of the cable 436. The compression wave transmitter shown in FIG. 10 is electrically operated and may be of any specific type such as a clapper, or a piezoelectric or magnetostrictive transducer, which is adapted to discharge compression waves such as sound.

Obviously, however, a transmitter adapted to discharge test energy in the form of electrical current could, instead, be employed with suitable modifications.

Apparatus 410 utilizes detection equipment 499 which is virtually identical to that of apparatus 10 of the first form of the present invention. However, the detection equipment does differ somewhat from that of apparatus 10. Such differences involve the circuitry for operation of the temperature sensor 463 and transmitter 470 and only that portion of the equipment which differs from detection equipment 99 of apparatus 10 is shown in FIG. 10, the remainder of the equipment being identical. As previously noted, the transmitter is mounted on the remote end of the core 439 of the cable 436. In the third form of the invention, the commutator 105 mounts a fourth brush type electrical connection 506 to which electrical conductor 132 is connected. A suitable temperature readout gauge is shown in 507. An electrical conductor 540 interconnects electrical connection 506 and is extended the full length of the core 439 of the cable 436 the remote end of which is connected to the transmitter 470. An electrical conductor 541 interconnects the transmitter and the electrical connection 106 of the commutator 105 adjacent to connection 506 extending through the core of the cable. This same connection 106 is connected to electrical conductor 122 thus completing this portion of the circuit from the pulse generator 103 through the battery 104.

Electrical conductor 542 interconnects conductor 132 and the electrical contact 106 of the commutator 105 in the center as viewed in FIG. 10. Electrical conductor 543 interconnects the central electrical contact 106 and the temperature sensor 463 extending internally of the core 439 of the cable 436. An electrical conductor 544 is connected to the temperature sensor and extends back through the core of the cable to the electrical contact 106 of the commutator on the far right as viewed in FIG. 10. Electrical conductor 545 interconnects the same electrical contact 106 and the temperature readout gauge 507. The temperature readout gauge is connected to conductor 137, as shown in FIG. 10.

As shown in FIG. 9, a zone of cooling is indicated at 550 and a plurality of paths of test energy at 555 for illustrative convenience as in the other forms of the invention.

OPERATION

The operation of the described embodiments of the subject invention and the practice of the methods thereof are believed to be clearly apparent and are briefly summarized at this point. As previously discussed, the objective in the operation of the method and apparatus of the present invention is the accurate detection of the thermal characteristics, both thermal conductivity and latent heat, of a subsurface formation. This objective is achieved in the method and apparatus of the present invention by permitting analysis of the subsurface formation in situ thereby avoiding interfering with the formation, as required by conventional methods and apparatus, in a manner which precludes the compilation of reliable data.

Figure 2:
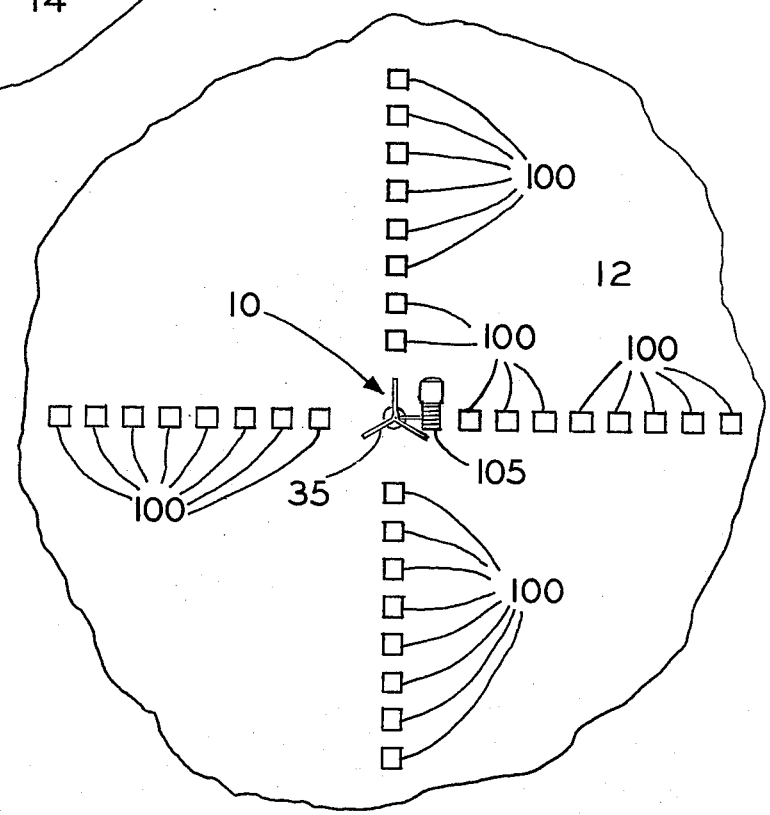
FIG. 2 is a schematic top plan view of the apparatus shown in FIG. 1.

Thus, the practice of the method of all three forms of the present invention calls for the mounting of the plurality of receivers 100 on the earth's surface 12, 212 and 412 along a pair of lines which intersect in right-angular relation extending laterally of the boreholes 13, 213 and 413 respectively. This array is shown with respect to apparatus 10 in FIG. 2. The precise number of receivers employed and the area covered depends, in part, on the depth of the formation to be studied and the distance between the transmitter and zone of cooling since, as can best be seen in FIG. 1, a sufficient number of receivers must be employed to detect test energy passing laterally of the zone.

The vessels 60 and 260 of apparatus 10 and 210 respectively, are filled with a predetermined quantity of suitable cryogenic material 69 and 269 having an extremely low temperature. Liquid nitrogen, liquid helium and liquid argon are excellently suited for this purpose having temperatures in the approximate range of from −452° Fahrenheit to −302° Fahrenheit. The cylindrical portions 61 and 261 of vessels 60 and 260 respectively operate to assist in maintaining the natural temperature of the cryogenic material so as to prevent it from being boiled off by the ambient temperature of the atmosphere. In the case of vessel 460 of apparatus 410, the insulating sheath 468 is removed from the solid bar 461 and the bar is immersed in such a cryogenic material until the temperature of the bar has been reduced to or near the temperature of the cryogenic material. Subsequently, the sheath is remounted about the bar to preserve its artificially very low temperature for operational use.

Thereafter, vessels 60, 260 and 460 are lowered by their respective hoist assemblies 35, 235, and 435 down their respective boreholes 13, 213 and 413 within the casings 20, 220 and 420. The heat conductive portions 65, 265 and 465 seat in the annular rings 23, 223 and 423 respectively. As can be seen in FIGS. 3 and 7, the electrical contacts 67 and 267 of vessels 60 and 260 engage their respective spring contacts 30 and 230 when the vessels have seated in the rings. In the case of vessel 460, no such contact is necessary since the transmitter 470 is mounted directly on the core 439 of the cable 436. However, as vessel 460 approaches its annular ring 423, the remote ends 428 of the stripping arms 427 contact the insulated cap 446 of the vessel and are motivated outwardly thereabout to engage and strip off the segmented portion 469 of the insulating sheath 468 so as to expose the conical portion 465 thereof for engagement with the ring. As can best be seen in FIG. 8, the stripping arms actually remove the segmented portion from the vessel as shown in dashed lines immediately prior to seating of the conical portion in the annular ring.

In the case of apparatus 210, the second vessel 280 rests upon the straps 270 of the first vessel 260 during lowering thereof into the borehole. Since, as can be seen in FIG. 7, the diameter of the first vessel is small enough to permit passage through the second annular ring 227, the first vessel is permitted to be lowered to seat in the first annular ring 223 as previously described. Since the second vessel 280 is of a predetermined larger diameter, it is adapted to seat in the second annular ring 227 after the first vessel has passed therethrough. Thus, two zones of cooling 350 and 351 are formed about the annular rings by the ambient temperature of the formation boiling off the cryogenic material carried by the respective vessels. The spacing of the rings is preferably such that the diameters of the zones of cooling at maximum size overlap a distance equal to the radii thereof, as best shown in FIG. 6, for purpose subsequently to be explained.

The highly heat conductive nature of the annular rings 23, 223, 227 and 423 and of portions 65, 265, 284 and 465 operate to draw the ambient heat from the fluid 26, 226 and 426 and from the formation adjacent thereto which has two results important in the practice of the method of the present invention. First, the fluid is rapidly frozen by the removal of such heat and similarly over a period of time the zones of cooling 150, 350, 351 and 550 of roughly spherical configuration are formed in the formation about the annular rings, as best shown in FIGS. 1, 6 and 9. The sizes of the zones of cooling depend upon the thermal characteristics of the formation and are a substantial factor in the operation of the method of the present invention. Second, the transfer of the ambient heat from the formation to the cryogenic material 69 and 269 borne by vessels causes such material to be boiled off over a period of time with the vapor liberated thereby permitted to escape through the vents 63 and 263 respectively. In the case of vessel 460 the ambient heat transfer simply causes the temperature of the bar 461 to approach that of the formation over a period of time. This too is a substantial factor in the practice of the method of the present invention, as will be seen.

The detection equipment 99, 299 and 499 is preferably activated immediately upon seating the vessels 60, 260, 280 and 460 in their respective annular rings 23, 223, 227 and 423. This is accomplished by activating the receivers 100, amplifier 101 and recorder 102 using their individual power source, not shown. Additionally, switches 121, 131 and 138 are closed to complete the electrical circuit 109. Thus, electrical current is supplied from the battery 104 through the circuit to the pressure transducers 68, 268, 290, temperature sensor 463 and pressure readout gauges 107, 307, 308 and temperature readout gauge 507 respectively. Thus, the pressure readout gauges can immediately be monitored to note the dissipation of cryogenic material by the heat of the formation.

Depending upon the type of pulse generator 103 employed, as previously noted, either automatically or on command the pulse generator is operated to discharge a pulse of electrical current to the transmitter and the amplifier. The pulse of current operates the transmitters 31, 231 and 470 respectively to discharge test energy therefrom. The simultaneous receipt of the pulse of current by the amplifier 101 causes a surge of power which the recorder 102 instantaneously records so as to indicate the precise relative time of test energy discharge from the transmitters.

Depending upon the type of transmitter employed, test energy in the form of electrical current, compression waves, or the like is discharged by the transmitters 31, 231 and 470 through the casings 20, 220 and 420 and into the formation about the lower ends 14, 214 and 414 of the boreholes 13, 213 and 413. The test energy travels along a plurality of paths, some of which are represented by paths 155, 355 and 555, through the formation and the forming zones of cooling 150, 350, 351 and 550 for detection by the receivers 100 on the earth's surface 12, 212 and 412, as shown in FIGS. 1, 6 and 9. With the detection equipment thus activated, the individual signals received by the receivers are transmitted through conductors 110 to the amplifier 101 for selected individual adjustment so as to establish usable signals for test purposes. These signals are individually recorded by the multichannel recorder 102 to provide a permanent record for subsequent analysis.

Depending upon the specific type of test energy employed, that is whether compression waves, electrical energy, or the like, and depending upon the structure and composition of the formation and the temperature to which it has been reduced, the transmission of such energy through the zones of cooling 150, 350, 351 and 550 will affect, in various ways, the test energy in a detectable manner. The detection of the effects of such transmission permits a determination on the surface as to when test energy received by a given receiver has passed through the zone of cooling. For example, the reduction in temperature of a given formation will, in certain circumstances, increase the electrical conductivity of the formation. In this case where the paths of test energy pass through the zones of cooling electrical conduction and therefore the amperage received by a given receiver will be increased above that for current not passing through the zones. In the case of the compression waves the effect may be somewhat different. The reduction in temperature of the formation may increase the density of that formation. Thus in this case where compression waves are employed as test energy, the velocity of waves following paths through the zones will be reduced in comparison with that of waves not traveling through the zones due to the increased density of the formation within the zones of cooling.

Regardless of the specific effect on the test energy, it is clear that the reduction of temperature within the zones of cooling will effect the test energy passing through the zones in a detectable manner as compared with the test energy not passing through the zones. It will be seen that all that is required is to note where such changes have occurred. The practice of the method is not dependent upon noting the degree and particular manner of such change.

The periodic discharge of test energy by the transmitters 31, 231 and 470 is preferably continued at least until their respective zones of cooling have reached maximum size. The data recorded by the multichannel recorder 102 thus establishes a permanent record for subsequent analysis of the maximum lateral dimensions of the zone of cooling. Since, as indicated, in most cases the zone of cooling takes a substantially spherical configuration having a center roughly coinciding with the annular ring, the volume of the zone can, in many cases, be calculated from the computed lateral dimensions, as will be seen. However, for purposes of accuracy, thermister readings are preferably continually made in the borehole during formation of the zone to determine or confirm the maximum vertical dimensions of the zone of cooling.

Where electrical current is employed as the test energy, the amperage of the energy received by the individual receivers 100 is recorded by the recorder 102 for subsequent analysis. Similarly, where compression waves are utilized as the test energy, the comparative time of receipt of the compression waves by the receivers is recorded by the recorder. In both cases, the previously discussed variation in energy received by the receivers will indicate which receivers received test energy which passed through the zone of cooling. By noting the locations of those receivers on the earth's surface, the depth of the annular ring and the depth of the transmitter, the lateral dimensions of the zone of cooling can be computed by trigonometric calculation. The vertical dimensions are calculated by the aforementioned thermister readings. The volume of the maximum size of the zone is then computed from this information.

Monitoring of the pressure readout gauge 107, in the case of apparatus 10, and of pressure readout gauges 307 and 308 in the case of apparatus 210 indicates when the pressure transducer 68 of apparatus 10 and the pressure transducers 268 and 290 of apparatus 210 have detected that all of the cryogenic material 69 and 269 contained in vessels 60, 260 and 280 has been boiled off by the ambient temperature of the formation. The calculation of the time required for such boiling off of the predetermined quantity of cryogenic material when compared with the sizes of the zones of cooling will provide indices of the latent heat of the formation providing still another dimension to the analysis of the thermal characteristics of the formation. Similarly, in the case of apparatus 410, monitoring of the temperature readout gauge 507 indicates when the temperature of the solid bar has reached a plateau and thus is about that of the formation. This information coupled with the volume of the zone of cooling 550 provides an index of the latent heat of the formation.

The method employed in the case of apparatus 210 calls for the creation of two such zones of cooling. While some of the test energy passes through both zones, experimentation and previous experience will permit the operator to judge, by the effect on the energy, the lateral dimensions of the zones and therefore calculate their maximum volumes. This method is of assistance in analyzing any variation in the thermal conductivity and/or latent heat of the formation under study. Thus, if one of the zones of cooling 350 or 351 reaches maximum size sooner than the other and/or if one of the zones achieves a greater maximum volume than the other zone of cooling, this indicates that there is a variation in thermal conductivity of the formation and/or that the latent heat of the formation varies to the extent that there is a heat flux through the formation. Similarly, if there is a variation in the time required for the ambient heat of the formation to boil off the predetermined quantities of cryogenic material 269 borne by the vessels 260 and 280, this will indicate that the latent heat of the formation within the two zones is different.

The temperature of the zones of cooling 350 and 351 formed by operation of the method and apparatus 210 of the second form of the present invention return to ambience relatively slowly, such as over a period of from several hours to several days after the cryogenic material 269 borne by vessels 260 and 280 has been boiled off. This is responsible for a variation in the practice of the method previously described. This variation calls for the vessels 260 and 280 to be refilled with cryogenic material and reinserted into the casing 220 for individual seating in their respective annular rings 223 and 227 a predetermined period of time after the original insertion. The test is thus repeated in an effort to determine if one of the zones of cooling is returning to ambience faster than the other. This is indicated upon conduction of the test energy through the zones of cooling determining initially what the comparative sizes of the zones of cooling are immediately upon insertion of the vessels into the casing and subsequently upon determining any variation in the maximum sizes of the newly formed zones of cooling. Thus, if the lower or first zone of cooling 350 returns to ambience faster than that above, this indicates that a heat flux is occuring in the formation from below.

Thus, the practice of the methods and apparatus of the present invention permit the conducting of geological surveys to determine, with a precision unachievable by conventional practices, the thermal characteristics, including thermal conductivity and latent heat, of a subsurface formation in situ avoiding the necessity of taking core samples which have proved highly unreliable.

Although the invention has been shown and described in what are conceived to be the most practical and preferred embodiments, it is recognized that departures may be made therefrom within the scope of the invention, which is not to be limited to the illustrative details disclosed.

Having described my invention, what I claim as new and desire to secure by Letters Patent is:

1. A method for detecting the thermal characteristics of a subsurface formation in situ comprising inserting cryogenic material into said formation to a predetermined position to produce a zone of cooling thereabout; conducting a plurality of paths of test energy, subject to detectable alteration by passage through a cooled medium, from a predetermined position spaced from the zone of cooling through and laterally of said zone of cooling; and individually detecting the paths along which said energy has been altered by passage through the zone of cooling to determine the size of said zone of cooling from such detection and the known position of energy discharge relative to the position of the cryogenic material to detect the thermal conductivity of the formation.

2. A method for detecting the thermal characteristics of a subsurface formation in situ comprising inserting cryogenic material into said formation to a predetermined position to produce a zone of cooling thereabout; conducting a plurality of paths of test energy, subject to detectable alteration by passage through a cooled medium, from a predetermined position spaced from the zone of cooling through and laterally of said zone of cooling; individually detecting the paths along which said energy has been altered by passage through the zone of cooling to determine the size of said zone of cooling from such detection and the known position of energy discharge relative to the position of the cryogenic material to detect the thermal conductivity of the formation; continuing to detect alteration of the test energy through detection of the maximum size reached by the zone until no further alteration is detectable to determine when the ambient temperature of the formation has returned the temperature of the zone of cooling to ambience; and recording the time required to return the temperature of said zone to ambience from said maximum size of the zone to determine the latent heat of the formation.

3. The method of claim 2 including employing a predetermined quantity of cryogenic fluid as the cryogenic material and recording the time required by the ambient temperature of the formation to boil off the quantity of material to determine the latent heat of the formation.

4. The method of claim 3 including drilling a borehole into said formation, discharging test energy from a position in the borehole remote from the surface and inserting said material into the borehole to a selected position intermediate the energy discharging position and the surface.

5. The method of claim 4 including taking temperature readings in the borehole through the zone of cooling to determine the vertical dimension of said zone.

6. A method for detecting the thermal characteristics of a subsurface formation in situ, including thermal conductivity and latent heat thereof, wherein a borehole has been drilled into the formation, comprising conducting test energy subject to alteration by low temperature along a plurality of paths through the formation from a selected position in the borehole remote from the surface; artificially withdrawing the heat from the formation with a predetermined volume of cryogenic material positioned in the borehole between said position of test conduction and the surface to form a zone of cooling through and about which the paths extend; individually sensing alteration in said energy at the surface for each of the paths incident to passage through said zone to determine the lateral dimensions of the zone; taking temperature readings in the borehole to determine the vertical dimension of the zone and thus the volume of the zone of cooling from said vertical and lateral dimensions to determine the thermal conductivity of the formation; and recording the time required for said material to be depleted by the ambient temperature of the formation for determination of the latent heat of the formation.

7. The method of claim 6 including using electric current as the test energy and recording at the surface the change in amperage of current passing through the zone relative to the amperage of current not passing through the zone.

8. The method of claim 6 including using compression waves as the test energy and recording at the surface the change in velocity of waves passing through the zone relative to those not passing through the zone.

9. The method of claim 6 including establishing two zones of cooling along the borehole through and about which the paths of test energy conduction extend for individual determination of the volumes of said zones and the times required for the ambient temperature of the formation to return the temperatures of the zones to ambience to determine variations in the thermal conductivity and latent heat of the formation.

10. The method of claim 9 including artificially withdrawing the heat from the formation a second time to establish two zones of cooling after the previous withdrawal but before the zones have been returned to ambient temperature at substantially the same positions for individual determination of the volumes of the zones and the times required for the zones to return to ambient temperature to determine any variation between said zones and therefore the amount of ambient heat supplied from the formation in upper and lower directions.

11. The method of claim 6 including using a super-cooled metal bar as the cryogenic material.

12. An apparatus for detecting the thermal characteristics of a subsurface formation in situ wherein a borehole has been drilled into the formation comprising means disposed in the borehole remote from the surface for conducting test energy subject to change by subjection to low temperature through said formation to the surface, means positioned in the borehole between said conducting means and the surface for withdrawing the ambient heat from the formation to form a zone of cooling in a position through and about which said test energy passes, and means mounted on the surface for detecting changes in the test energy incident to the passage thereof through said zone to permit determination of the size of the zone thereby to determine the characteristics of thermal conductivity of said formation.

13. An apparatus for detecting the thermal characteristics of a subsurface formation in situ wherein a borehole has been drilled into the formation comprising means disposed in the borehole remote from the surface for conducting test energy subject to change by subjection to low temperature through said formation to the surface; means positioned in the borehole between said conducting means and the surface for withdrawing the ambient heat from the formation to form a zone of cooling in a position through and about which said test energy passes, and wherein the heat withdrawing means includes a vessel of cryogenic material adapted to be selectively positioned in the borehole and said heat withdrawing means further includes a seat member of heat conductive material positioned in the borehole in a predetermined location and adapted to receive said vessel and to conduct the ambient heat of the formation to the cryogenic material borne thereby to form a zone of cooling in the formation about the seat member; and means mounted on the surface for detecting changes in the test energy incident to the passage thereof through said zone to permit determination of the size of the zone thereby to determine the characteristics of thermal conductivity of said formation.

14. The apparatus of claim 13 in which the vessel is a supercooled bar of heat conductive material.

15. The apparatus of claim 14 in which the bar is enclosed in a thermally insulating sheath and means are borne internally of the casing for stripping a portion of said sheath from the bar prior to engagement with the seat member.

16. The apparatus of claim 13 in which the material borne by the vessel is a liquid subject to boiling off by the heat of the formation and means are mounted on the vessel for detecting when said liquid has been boiled off.

17. The apparatus of claim 16 in which the conducting means includes an electric current discharging device positioned in the borehole so as to locate the seat member intermediate said device and the surface.

18. The apparatus of claim 16 in which the conducting means includes a compression wave discharging device positioned in the borehole so as to locate the seat member intermediate said device and the surface.

19. An apparatus for detecting the characteristics of thermal conductivity of a subsurface formation in situ wherein a borehole has been drilled into the formation, the apparatus comprising a casing, having a sealed lower end portion, receivable in the borehole; an annular ring of heat conductive material mounted in the casing in predetermined spaced relation to the lower end portion thereof and in heat transferring relation to the formation; a transmitter mounted on the lower end portion of the casing adapted to transmit test energy, subject to change by passage through a cooled medium, along a plurality of paths through the formation to the surface; a vessel, having a heat conductive portion and an insulated portion, adapted to be rested in the annular ring with the heat conductive portion in heat transferring engagement therewith; a predetermined quantity of cryogenic fluid carried by the vessel and having the capacity of extracting heat from said formation in the path of the test energy by boiling off in the presence of heat transmitted thereto from the formation when the vessel is rested in the annular ring; means borne by the vessel for detecting when said fluid has been boiled off by the heat of the formation; and means disposed at the surface for receiving the test energy individually along said paths and recording changes therein incident to passage through the portion of the formation cooled by heat extraction.

20. The apparatus of claim 19 in which the receiving and recording means includes an array of energy sensors disposed at spaced increments on the surface radiating laterally from the borehole covering an area of sufficient size to receive energy transmitted along paths passing both through the cooled portion of the formation and laterally thereof.

21. The apparatus of claim 20 in which the receiving and recording means further includes a strip chart recorder having the capacity individually to record the energy detected by each of the sensors for subsequent analysis.

22. The apparatus of claim 21 in which the detecting means includes a pressure sensitive transducer mounted in the heat conductive portion of the vessel in communication with the cryogenic fluid received therein.

23. The apparatus of claim 22 in which a readily freezable fluid is disposed about the casing in the borehole reaching a level above the annular ring.

24. The apparatus of claim 23 in which a second annular ring of heat conductive material is mounted in the casing in spaced relation to the first annular ring and a second vessel adapted to receive fluid for heat extraction from the formation is adapted to be seated in said second annular ring to form a second zone of cooling in the path of the test energy.

25. A method for detecting the thermal characteristics of a subsurface formation in situ comprising inserting cryogenic material into said formation to a predetermined position to produce a zone of cooling thereabout; conducting a plurality of paths of test energy, subject to detectable alteration by passage through a cooled medium, from a predetermined position spaced from the zone of cooling through and laterally of said zone of cooling; individually detecting the energy in said paths subsequent to passage through and laterally of said zone; and recording the energy altered by passage through the zone in comparison with that not altered to determine the thermal conductivity of the formation as indicated by the size of said zone determined from the recorded energy and the known distance between the position of energy discharge and the position of the cryogenic material.

26. A method for detecting the thermal characteristics of a subsurface formation in situ comprising inserting cryogenic material into said formation to a fixed position to produce a zone of cooling in the formation thereabout; emitting test energy subject to detectable reduction by passage through the zone of cooling from a position spaced from the zone of cooling; individually detecting the energy conducted along a plurality of paths of predetermined relation from said position, some of which extend through the zone and others of which extend past the zone in laterally spaced relation thereto; and comparing the energy conducted through the zone with the energy conducted passed the zone to determine the thermal conductivity of the formation as indicated by the size of said zone.

27. A method for detecting the thermal characteristics of a subsurface formation in situ comprising the steps of:

A. artifically withdrawing a predetermined amount of ambient heat from the formation at a predetermined position thereby to reduce the temperature of an affected portion of the formation about said position;

B. conducting test energy, subject to alteration by passage through a cooled medium, through and about said affected portion;

C. detecting the energy altered by passage through said affected portion to determine the maximum size of the affected portion of the formation; and D. timing the interval between heat withdrawal and said affected portion reaching maximum size.

28. The method of claim 27 including continuing to detect said energy until the ambient heat of the formation returns said affected portion of the formation to ambient temperature; and timing the interval between said affected portion reaching maximum size and said affected portion being returned to ambient temperature.

29. An apparatus for detecting the thermal characteristics of a subsurface formation in situ wherein a borehole has been drilled into the formation comprising means positioned in the borehole remote from the surface for conducting test energy, subject to change by passage through a cooled medium, through said formation to the surface; a vessel adapted to receive cryogenic material; means mounted in the borehole between said conducting means and the surface for receiving said vessel and establishing heat withdrawing communication between cryogenic material received in said vessel and the formation about said position to form a zone of cooling through and about which said test energy passes; and means mounted on the surface for detecting changes in the test energy incident to the passage thereof through said zone to permit determination of the size of the zone thereby to determine the characteristics of thermal conductivity of said formation.

* * * * *

UNITED STATES PATENT AND TRADEMARK OFFICE
CERTIFICATE OF CORRECTION

PATENT NO. : 3,938,383
DATED : February 17, 1976
INVENTOR(S) : Wayne L. Sayer

It is certified that error appears in the above-identified patent and that said Letters Patent are hereby corrected as shown below:

Column 9, Line 50, delete "446" and insert "466".

Column 11, Line 40, delete "446" and insert "466".

Signed and Sealed this fourth Day of May 1976

[SEAL]

Attest:

RUTH C. MASON
*Attesting Officer*

C. MARSHALL DANN
*Commissioner of Patents and Trademarks*